United States Patent [19]

Goliaszewski

[11] Patent Number: 4,781,862

[45] Date of Patent: Nov. 1, 1988

[54] PROCESS FOR THE PREPARATION OF ANTHRAQUINONE

[75] Inventor: Alan E. Goliaszewski, Palmyra, N.J.

[73] Assignee: Montvale Process Company, Inc., Westport, Conn.

[21] Appl. No.: 883,232

[22] Filed: Jul. 8, 1986

[51] Int. Cl.$^4$ ............ C07C 50/18; B01J 21/02; B01J 21/14; B01J 27/02
[52] U.S. Cl. ............ 260/369; 502/102; 502/162; 502/168; 502/208; 502/508
[58] Field of Search ............ 260/369; 502/162, 168, 502/208, 508, 102

[56] References Cited

U.S. PATENT DOCUMENTS

| | | | |
|---|---|---|---|
| 2,401,225 | 5/1946 | Caesar et al. | 260/369 |
| 4,036,860 | 7/1977 | Engelbach et al. | 260/369 |
| 4,379,092 | 4/1983 | Devic | 260/369 |
| 4,400,324 | 8/1983 | Brima et al. | 260/369 |
| 4,411,818 | 10/1983 | Reater et al. | 260/369 |
| 4,444,904 | 4/1984 | Ryu | 502/162 |
| 4,459,234 | 7/1984 | Kawamato et al. | 260/369 |

FOREIGN PATENT DOCUMENTS

| | | | |
|---|---|---|---|
| 57-31637 | 2/1982 | Japan | 260/369 |
| 57-70833 | 5/1982 | Japan | 260/369 |
| 57-70832 | 5/1982 | Japan | 260/369 |

OTHER PUBLICATIONS

Kirk-Othmer, Encyclopedia of Chemical Technology 1978, 3rd ed., vol. 2, pp. 702-707.
Hino, J. Chem. Soc., Chem. Commun., 1985, p. 112.

*Primary Examiner*—Glennon H. Hollrah
*Assistant Examiner*—Raymond Covington
*Attorney, Agent, or Firm*—William C. Long; Bruce M. Collins

[57] ABSTRACT

Anthraquinone is produced by reacting phthalic anhydride in the vapor phase over a catalyst which may be an oxide of the Group 4b metals zirconium, hafnium, and titanium, the Group 5b metals niobium, tantalum, and vanadium, or the rare earths cerium and thorium such oxides, preferably being treated with sulfuric acid and calcined. Substituted anthraquinones may be produced by employing the corresponding substituted phthalic anhydrides.

13 Claims, No Drawings

PROCESS FOR THE PREPARATION OF ANTHRAQUINONE

PRIOR ART

Anthraquinone and its derivatives are widely used in the dye industry and find other applications in the manufacture of hydrogen peroxide and in the paper pulp industry. Anthraquinone is produced industrially by several processes, principally by oxidizing anthracene or from the reaction of butadiene with naphthalene-derived naphthaquinone followed by an oxidation. It can also be produced from the reaction of phthalic anhydride with benzene.

Anthracene is available in small quantities from coal tar and is used to make anthraquinone, but purification of the anthracene feed is difficult and expensive, so that this process is undesirable, even though it has been widely used. Another disadvantage of the process is that the supply of anthracene from coal tar is uncertain and it is expected in the future that its use as a source for anthraquinone will be significantly reduced.

At one time, phthalic anhydride and benzene were reacted commercially in a Friedel-Craft reaction using aluminum chloride in order to produce an intermediate compound, ortho-benzoylbenzoic acid, which is then converted by acid treatment to anthraquinone. The process consumed large quantities of aluminum chloride and had other disadvantages. Consequently, it is no longer used industrially and new processes have been sought for preparation of anthraquinone.

An alternative to the use of aluminum chloride is found in U.S. Pat. No. 4,379,092. Hydrogen fluoride and boron trifluoride are used to react phthallic anhydride with benzene in the liquid phase. The process consumes substantial amounts of boron trifluoride and is run at below ambient temperatures, thus requiring refrigeration.

Other processes have been proposed. See Kirk-Othmer, Encyclopedia of Chemical Technology, John Wiley & Sons, 1978, 3rd ed., vol. 2, p. 702-707. Among these are the reaction of 1,4 naphthoquinone with 1,3 butadiene followed by the oxidation of tetrahydroanthraquinone to form anthraquinone. Another method is the oxidation of diphenyl methane derivatives to the intermediate ortho benzoyl benzoic acid, which is subsequently converted to anthraquinone, as shown in U.S. Pat. No. 4,036,860.

The reaction of phthalic anhydride and benzene in the presence of various catalysts also has been proposed. The catalysts disclosed include silica plus amphoteric metal oxides, including zirconium oxide, as seen in U.S. Pat. No. 2,401,225. Titanium and/or tin oxides have been proposed as catalysts for this reaction in U.S. Pat. No. 4,459,234, which suggests that sulfuric acid treatment may be helpful in improving the activity of these catalysts. A group of Japanese published applications also show metal oxides used as catalysts for this reaction. Japanese Kokai No. 57-70833 discloses the use of boria as the principal metal oxide, in combination with titanium, zirconium, tin, aluminum, tungsten, or lead oxides. A titania-boria catalyst is shown in Example 1 to convert phthalic anhydride in a nitrogen carrier gas to anthraquinone. Japanese Kokai No. 57-70832 is directed specifically to the use of the combination of silica, alumina and boria. In Example 1 phthalic anhydride in a nitrogen carrier gas is passed over such a catalyst. Still another Japanese Kokai No. 57-31637 discloses the use of magnesium and silicon as oxides or sulfates, with many other metal oxides suggested as additives, including zirconium oxide.

Hino, et al. (in J. Chem. Soc., Chem. Commun., 1985, p. 112) disclosed a super acid catalyst prepared by contacting $Zr(OH)_4$ with sulfuric acid followed by calcination as useful in the acylation of toluene with benzoic anhydride to produce methyl benzophenone. Such super acid catalysts are considered to be among the most acidic solid materials presently available.

Despite the many disclosures of processes by which anthraquinone may be prepared and the commercial interest in such processes, those skilled in the art continue to search for improved methods of preparation. The present invention discloses an improved process by which anthraquinone may be prepared from phthalic anhydride alone by a vapor phase reaction over a catalyst.

SUMMARY OF THE INVENTION

Anthraquinone is produced by reacting two molecules of phthalic anhydride in the vapor phase over a catalyst. The catalyst will consist of at least one oxide from the group consisting of the Group 4b metals zirconium, hafnium, and titanium, the Group 5b metals niobium, tantalum, and vanadium, or the rare earths cerium and thorium.

In one embodiment of the invention, such oxides are treated to incorporate sulfate or phosphate moieties; using for example sulfuric or phosphoric acids and then calcined. Such catalysts are termed "super acid" catalysts.

The reaction is carried out at a temperature of about 350° to 550° C., preferably 420° to 480° C. and at a pressure of about 0.01 to 200 bar, preferably 1-3 bar, said temperature and pressure being selected to maintain the phthalic anhydride in the vapor phase.

The anthraquinone produced is separated from the reactor effluent gases, for example by condensation, and the unconverted phthalic anhydride, along with some of the carbon dioxide by-product as a carrier gas, is recycled to the reactor. Substituted anthraquinones may be produced by reacting two molecules of the corresponding substituted phthalic anhydride over the catalysts of the invention.

DESCRIPTION OF THE PREFERRED EMBODIMENTS

Catalysts

Although the prior art suggests that phthalic anhydride will react with benzene to form anthraquinone, it has now been found that in the presence of the catalysts of the invention benzene does not react with phthalic anhydride. Instead, two molecules of phthalic anhydride actually react in a vapor phase reaction even if benzene is present.

Various metal oxides have been found to be useful, including the Group 4b metals zirconium, hafnium, and titanium, the Group 5b metals niobium, vanadium, and tantalum, or the rare earths cerium and thorium. Zirconium oxide is particularly useful. These metal oxides may be used alone or in combination, but preferably they are converted to super acid catalysts by reaction with acids to incorporate sulfate or phosphate moieties, particularly sulfuric or phosphoric acids, followed by calcination in air at temperatures in the range of 500° to 700° C., preferably 600° to 620° C.

When treated with sulfate or phosphate moieties the catalysts may be called "super acid" catalysts. As used here, the term "super acid" catalyst refers to materials having a Hammett acidity of less than −12.0, R. Gillespie and T. Peel, J. Am. Chem. Soc. 95, 5173 (1973). After treating, the catalysts are calcined to produce a catalyst having an acid strength of less than −16.04, as measured photometrically by color change of weak bases (e.g. 2,4-dinitrofluoro benzene) when coordinated to acid sites on the catalyst.

The following example will provide a typical preparation of a zirconium super acid catalyst useful in the preparation of anthraquinone.

EXAMPLE 1

Catalyst Preparation

Zirconyl chloride octahydrate (504 gm) is dissolved in 1.65 liters of deionized water and mixed with 0.4 liters of 28% ammonium hydroxide solution over a period of 30 minutes. Insoluble $Zr(OH)_4$ precipitates, after which the solids are recovered by filtration and then reslurried four times with 1.2 liter increments of deionized water. The washed solids are dried at 80° C. for 15 hours. Then, they are stirred with 0.5 liters of 1N sulfuric acid for three hours and recovered by filtration. The solids are calcined at 620° C. in air for three hours, after which time the catalyst is ready for use. Typically the catalyst will contain 51.2–1.4 wt. % sulfur and have a surface area of 100–140 $m^2$/gm.

Although in the foregoing example the catalyst was prepared from zirconyl chloride, it is also feasible to use zirconium oxides, $ZrO_2$, from other water soluble sources, such as zirconyl nitrate hydrate, zirconium (IV) nitrate, and zirconium(IV) chloride.

Sulfuric acid is the preferred acid but other sulfate sources could be used, such as chlorosulfuric acid, fluorosulfuric acid, sulfur trioxide, sulfur dioxide plus oxygen, or solid ammonium sulfate. The concentration of the acid may vary from 0.1 to about 5 molar; at higher concentrations zirconium(IV) is dissolved. The amount of acid needed preferably is greater than that needed to provide sulfate species, the amount in the finished catalyst being generally about 0–2 wt. percent sulfur. Contacting of the zirconium oxide and the acid typically will require about 1 to 200 minutes, but is not believed to be critical.

If phosphate moieties are used, they may be derived from phosphoric acid, phosphorous oxychloride, ortho phosphate esters, and the like.

It has been found that the calcination temperature is an important factor in establishing the activity of the resulting catalyst for producing anthraquinone from phthalic anhydride. Although temperatures in the range of 400° to 750° C. may be used, the maximum temperature preferably will be in the range of 550° to 650° C., especially 600° to 620° C. The optimum temperature may vary, depending upon the metal oxide and the acid used.

The catalyst may be used in the powdered form produced in Example 1, or it may be pelletized, extruded, or otherwise compacted for use in commercial applications.

Promoters are not required, but may include such elements as the oxides of molybdenum, tungsten, chromium, or manganese.

Process

It is unique to the process of the invention that phthalic anhydride is the only molecular species required, in view of much prior art suggesting that phthalic anhydride reacts with benzene to produce anthraquinone. However, benzene can contribute to deactivation of the catalyst by being a substrate for coking processes in this acid environment and provides a source of hydride species for byproduct formation. Consequently, even though benzene could be present as a carrier, even if the reaction is principally between two molecules of phthalic anhydride, nevertheless it is preferred that benzene not be present. A carrier gas would be desirable however and, since carbon dioxide is a by-product of the reaction and thus readily available, it is preferred. Other carriers which may be used include inert gases, such as nitrogen, argon, helium, and the like. The amount of the carrier will depend upon a number of factors, such as the reactor pressure and temperature, but generally the gaseous feed to the reaction will contain about 0.1 to 5 mol %. phthallic anhydride.

The reaction may be carried out in a batchwise or continuous manner. The temperature and pressure will be established to maintain the phthalic anhydride in the vapor phase as well as to provide conditions under which the reaction proceeds quickly and efficiently. The temperature may be between about 350° and 550° C., while the pressure may be between about 0.01 and 200 bar. The conditions will be selected to maintain phthalic anhydride in the vapor phase and preferably to prevent product anthraquinone from condensing. If carried out in a batch reactor the catalyst will be preheated and then contacted with the feed as at the selected temperature and pressure for a period of up to 3 hours. Conveniently, the reaction is carried out continuously, so that the catalyst is placed in a vessel and contacted with a flowing stream of phthalic anhydride in the carrier gas. A contact time of about 0.1 to 100 minutes may be used. The exiting gases may be cooled to condense and separate the anthraquinone product, after which the carbon dioxide and any other by-products may be recycled or disposed of.

The following example illustrates one method of carrying out the process of the invention.

EXAMPLE 2

The super acid catalyst of Example 1 is pressed to form wafers, which are broken up to 4–12 mesh particles for use. A charge of 30 gms of catalyst particles is placed in a 1.91 cm o.d. stainless steel tube 68.6 cm long between 20 gm. sections of alpha-alumina inert particles. The catalyst is heated to about 450° C. and then 200 cc/min of a feed stream containing about 3.3 mol % of phthalic anhydride in nitrogen is introduced at 220° C. The gas stream leaving the reactor tube is cooled to about 0° C. so that the anthraquinone is condensed. The solid product is dissolved in dimethylformamide for analysis by gas chromatograph. The analysis indicates a conversion of 81% of the phthalic anhydride, with a selectivity to anthraquinone of 65%. By-products include minor amounts of benzophenone, fluorenone, thiophthalic anhydride, and o,o-carbonylbenzoic anhydride.

EXAMPLE 3

Titanium chloride (250 g) is slowly added to 1.25 liters of deionized water. This solution is heated to 100°

C. and 0.745 L of 28 wt. % ammonium hydroxide solution is added. The insoluble titanium hydroxide is collected by filtration and washed with four 0.50 liter increments of water. This Ti(OH)$_4$ is stirred gently with 0.40 liters of 1N H$_2$SO$_4$ for three hours. The solids are collected by filtration, dried at 80° C. for 15 hours, and calcined in air at 525° C. This material is pressed to form wafers and broken to form 4–12 mesh particles, 30 g of which are charged to the reactor described in example 2. At the same reaction conditions as example 2, analysis of products indicates a phthalic anhydride conversion of 18%, with a selectivity to anthraquinone of 56%.

Although acid-treated catalysts are preferred, the untreated metal oxides may also be used, as the following two examples demonstrate.

EXAMPLE 4

Untreated zirconium oxide that contained no sulfate species is prepared by the calcination of zirconium hydroxide at 620° C. in air. The Zn(OH)$_4$ is prepared by hydrolysis of zirconyl chloride as described in example 1. The material is pressed into wafers and broken to 4–12 mesh particles for use. Catalyst charge and reaction conditions are the same as in example 2. Analysis indicates a conversion of 13% phthalic anhydride with an anthraquinone selectivity of 57%. Byproducts were the same as in example 2.

EXAMPLE 5

Untreated titanium oxide is prepared by calcination of Ti(OH)$_4$ using the method described in example 4 at 525° C. in air. This material (30 g) is utilized in a reaction under conditions identical to those described in example 2. Analysis of products indicates a 5% conversion of phthalic anhydride with a selectivity to anthraquinone of 14%.

The following two examples show that two phthalic anhydride molecules react with each other to produce anthraquinone.

Example 6

A charge of 30 g of the super acid catalyst described in example 1 is placed in the reactor described in example 2 below a pre-heat section of 45 g of inert, low surface area alpha-alumina. The catalyst and alumina are heated to 450° C. and a feed stream of a 5% molar solution of phthalic anhydride dissolved in warm toluene (80° C.) is pumped into the top of the reactor column at a rate of 3.0 cc min$^{-1}$. Carbon dioxide is fed separately at a rate of 200 cc min$^{-1}$. Products are collected by cooling the exit gases to 0° C. Analysis indicates a 62% conversion of phthalic anhydride with a selectivity to anthraquinone of 36%.

This result demonstrates that toluene has not reacted with phthalic anhydride to form methyl anthraquinone and consequently, the product has been derived from two molecules of phthalic anhydride. Byproducts include a ortho-benzoylbenzaldehyde, benzophenone, fluorenone, thio-phthalic anhydride, di(methylbenzoyl)benzene, dimethyldiphenyl, and o,o-carbonylbenzoic anhydride.

EXAMPLE 7

A charge of 30 g of the catalyst of Example 1 is placed in the same reactor below a pre-heat section of 45 g of inert low surface area alpha alumina. The catalyst and alumina are heated to 450° C. and a feed stream of a 5 mol % solution of phthalic anhydride dissolved in warm (80° C.) fully deuterated toluene is pumped into the top of the reactor at a rate of 2 cc per minute. Carbon dioxide is fed at a rate of 240 cc per minute. The effluent gases are cooled to 0° C. to condense the products of the reaction. Analysis indicates a 60% conversion of phthalic anhydride with a 32% selectivity to anthraquinone. Minor by-products are fluorenone and benzophenone. The anthraquinone is found by gas chromatograph/mass spectral analysis to contain less than 1 deuterium replacement of hydrogen, which is equivalent to measurement of the feed phthalic anhydride, indicating that the anthraquinone was derived from two molecules of phthalic anhydride and not from the reaction of phthalic anhydride and toluene.

EXAMPLE 8

The experiment of Example 6 is repeated, except that a 4 mol % solution of 5-methyl phthalic anhydride dissolved in benzene is fed at 450° C. to the reactor at a rate of 3.0 cc per minute. Carbon dioxide is fed at a rate of 200 cc per minute. The effluent gases are cooled to 0° C. to condense the products. Analysis of the products indicates an 11% conversion of phthalic anhydride, with a 58% selectivity to dimethyl anthraquinone (two isomers).

EXAMPLE 9

Thorium nitrate tetrahydrate (276 g) is dissolved in 1.5 liters of deionized water and then hydrolyzed with 135 g of 28 wt. % ammonium hydroxide solution. The precipitated thorium hydroxide is filtered and washed with five 0.5 liter increments of water. The washed solids are dried in air and calcined in air at 575° C. for three hours to produce a thorium oxide catalyst. Thirty grams of the calcined catalyst is charged to the reactor of Example and the reaction of Example 2 repeated, with a good yield of anthraquinone obtained.

EXAMPLE 10

The catalyst preparation of Example 1 is repeated except that 0.5 liters of 1N phosphoric acid is mixed with the zirconium hydroxide instead of the sulfuric acid of Example 1. Again the treated solids are finished by calcining at 620° C. in air for 3 hours. When tested as in Example 2 by feeding phthalic anhydride in nitrogen a good yield of anthraquinone is obtained.

What is claimed is:

1. A process for the production of anthraquinone comprising: reacting two molecules of phthalic anhydride in the vapor phase, in the substantial absence of benzene, to form anthraquinone and carbon dioxide in the presence of a catalyst consisting of oxides of at least one member of the group of Group 4b metals zirconium, hafnium, and titanium, the Group 5b metals niobium, tantalum, and vanadium, or the rare earths cerium and thorium at a temperature in the range of 350°–550° C. and a pressure in the range of 0.01–200 bar, said temperature and pressure being selected to maintain the phthalic anhydride in the vapor phase.

2. The process of claim 1 wherein the catalyst of step (a) is treated with a source of sulfate or phosphate moieties and calcined at a temperature in the range of 400–750° C.

3. The process of claim 2 wherein said catalyst is sulfuric acid treated and has a Hammett acid strength of less than −16.04.

4. The process of claim 2 wherein the catalyst is zirconium oxide.

5. The process of claim 2 wherein the catalyst is titanium oxide.

6. The process of claim 1 wherein the temperature is in the range of 420°–480° C.

7. The process of claim 1 wherein the pressure is in the range of 1–3 bar.

8. The process of claim 1 further comprising the step of recycling unconverted phthalic anhydride and carbon dioxide to step (a).

9. The process of claim 2 wherein the calcination temperature is in the range of 550°–650° C.

10. A process for the production of lower alkyl substituted anthraquinones comprising:
(a) reacting two molecules of the corresponding lower alkyl substituted phthalic anhydride to form the desired substituted anthraquinone and carbon dioxide in the presence of a catalyst consisting of the oxides of at least one member of the group of Group 4b metals zirconium, hafnium, and titanium, the Group 5b metals niobium, tantalum, and vanadium, or the rare earths cerium and thorium, in the substantial absence of benzene, at a temperature in the range of 350°–550° C. and a pressure in the range of 0.01–200 bar, said temperature and pressure being selected to maintain the lower alkyl phthalic anhydride in the vapor phase;
(b) separating the lower alkyl substituted anthraquinone produced in step (a).

11. The process of claim 1 wherein the catalyst is hafnium oxide.

12. The process of claim 1 wherein the catalyst is niobium oxide.

13. The process of claim 1 wherein the ctalyst is cerium oxide.

* * * * *